(12) United States Patent
Laikhter et al.

(10) Patent No.: US 7,956,169 B1
(45) Date of Patent: Jun. 7, 2011

(54) SYNTHESIS OF NOVEL AZO-DYES AND THEIR USE IN OLIGONUCLEOTIDE SYNTHESIS

(75) Inventors: Andrei Laikhter, Lexington, MA (US); Suresh C. Srivastava, Burlington, MA (US); Naveen P. Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 0 days.

(21) Appl. No.: 12/816,527

(22) Filed: Jun. 16, 2010

(51) Int. Cl.
*C09B 56/16* (2006.01)
*C09B 29/40* (2006.01)
*C12Q 1/68* (2006.01)

(52) U.S. Cl. ............. 534/611; 534/774; 534/777; 435/6
(58) Field of Classification Search .................. None
See application file for complete search history.

(56) References Cited

U.S. PATENT DOCUMENTS

| | | | | |
|---|---|---|---|---|
| 2,464,785 | A | * | 3/1949 | Thompson ............ 534/606 |
| 3,681,320 | A | * | 8/1972 | Franklin ............... 534/576 |
| 3,956,264 | A | * | 5/1976 | Raue et al. ............ 534/606 |
| 4,826,976 | A | * | 5/1989 | Borror et al. .......... 544/58.4 |
| 4,927,917 | A | * | 5/1990 | Krongauz et al. ...... 534/567 |
| 6,218,072 | B1 | * | 4/2001 | Otaguro et al. ........ 430/270.21 |
| 7,019,129 | B1 | | 3/2006 | Cook et al. |
| 7,439,341 | B2 | | 10/2008 | Laikhter et al. |
| 7,803,536 | B2 | * | 9/2010 | Laikhter et al. ....... 435/6 |
| 2006/0177857 | A1 | | 8/2006 | Berry et al. |
| 2008/0221343 | A1 | * | 9/2008 | Schwartz et al. ....... 549/550 |

FOREIGN PATENT DOCUMENTS

| | | | |
|---|---|---|---|
| DE | 19649971 | * | 5/1998 |
| EP | 840307 | * | 5/1998 |
| JP | 63-129346 | * | 6/1988 |

OTHER PUBLICATIONS

Kiprianov, A..I., "Absorption Spectra of Organic Dyes Containing Two Chromophores", Russian Chemical Reviews, 40(7), 594-607, 1971.*
Kiprianov, A.I. et al., Cyanine Dyes With Two Congugated Chromophores VII., Chemical Abstracts, 70:79135, 1969.*

* cited by examiner

*Primary Examiner* — Fiona T Powers
(74) *Attorney, Agent, or Firm* — Hamilton, Brook, Smith & Reynolds, P.C.

(57) ABSTRACT

The invention provides a novel group of azo quencher compositions that are useful as quenchers of fluorescence and to methods for making and using them. The quenchers contain an azo bond and 1,3,3-trimethyl-2-methyleneindoline ring system. The quenchers can be derivatized to facilitate their conjugation to a variety of biologically relevant compounds, including lipids, nucleic acids, peptides, proteins, and the like.

24 Claims, 2 Drawing Sheets

SYNTHESIS OF NOVEL AZO-DYES AND THEIR USE IN OLIGONUCLEOTIDE SYNTHESIS

BACKGROUND OF THE INVENTION

Light quenching processes that rely on the interaction of two dyes as their spatial relationship changes can be used in convenient processes for detecting and/or identifying nucleotide sequences and other biological phenomena. In one such method the change in fluorescence of a fluorescent donor or quencher can be monitored as two oligonucleotides (one containing a donor and one containing a quencher) bind to each other through hybridization. The binding can be detected without intervening purification steps that separate unhybridized from hybridized oligonucleotides.

Another method for detecting hybridization using fluorophores and quenchers is to link fluorescent donors and quenchers to a single oligonucleotide such that there is a detectable difference in fluorescence when the oligonucleotide is unhybridized as compared to when it is hybridized to its complementary sequence. For example, a partially self-complementary oligonucleotide designed to form a hairpin can be labeled with a fluorescent donor at one end and a quencher at the other end. Intramolecular annealing into the hairpin form can bring the donor and quencher into sufficient proximity for fluorescent quenching to occur. Intermolecular annealing of such an oligonucleotide to a target sequence disrupts the hairpin, which increases the distance between the donor and quencher and results in an increase in the fluorescent signal of the donor.

However, oligonucleotides are not required to have hairpins for this later method to work efficiently. The fluorophore and quencher can be placed on an oligonucleotide such that when it is unhybridized and in a random coil conformation, the quencher is able to quench fluorescence from the fluorophore. Once the oligonucleotide hybridizes to a complementary nucleotide sequence it becomes more extended and the distance between the fluorophore and quencher is increased, resulting in increased fluorescence.

Oligonucleotides labeled in a similar manner can also be used to monitor the kinetics of PCR amplification. In one version of this method the oligonucleotides are designed to hybridize to the 3' side ("downstream") of an amplification primer so that the 5'-3' exonuclease activity of a polymerase digests the 5' end of the probe, cleaving off one of the dyes. The fluorescence intensity of the sample increases and can be monitored as the probe is digested during the course of amplification.

Similar oligonucleotide compositions find use in other molecular/cellular biology and diagnostic assays, such as in end-point PCR, in situ hybridizations, in vivo DNA and RNA species detection, single nucleotide polymorphism (SNPs) analysis, enzyme assays, and in vivo and in vitro whole cell assays.

Perhaps the most common mechanism of fluorescent quenching is known as FRET (fluorescent resonance energy transfer). For FRET to occur a fluorescent donor and a fluorescent quencher must be within a suitable distance for the quencher to absorb energy from the donor. In addition, there must be overlap between the emission spectrum of the fluorescent donor and the absorbance spectrum of the quencher. This requirement complicates the design of probes that utilize FRET because not all potential quencher/donor pairs can be used. For example, the quencher known as Iowa Black FQ (Laikhter, A., et al., U.S. Pat. No. 7,439,341), which absorbs light in the wavelength range of about 500-560 nm, can quench the fluorescent light emitted from the fluorophore, fluorescein, which fluoresces maximally at about 520 nm. The quencher known as BHQ-2 (compound 1) quencher (Cook, R. M., et al., U.S. Pat. No. 7,019,129), which absorbs light in the wavelength range of about 550-600 nm, can quench the fluorescent light emitted from the fluorophore, Cy3, which fluoresces maximally at about 570 nm. In contrast, the quencher BHQ-3 or BlackBerry (compound 2) quenchers (Berry, D. A., et al., US Patent application US 2006/0177857 A1), which absorbs light in the wavelength range of about 630-700 nm would be almost completely ineffective at quenching the fluorescence of fluorescein through FRET but would be quite effective at quenching the fluorescence of the fluorophore known as Cy5 which fluoresces at about 670 nm. In general, the number of quenchers known that are capable of quenching the fluorescence of any given fluorophore is quite limited. For example with fluorescein, only a limited number of suitable quenchers are known and they are quite expensive to purchase commercially. Because fluorescein is one of the most commonly used fluorophores, new quenchers that can quench fluorescent light in the 520 nm range of fluorescein are needed. Similarly, quenchers for other known fluorophores are also needed.

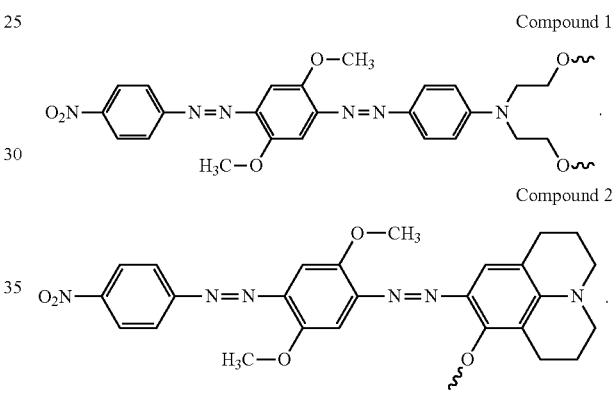

Compound 1

Compound 2

Ideally, new quenchers will not fluoresce so that background fluorescence is minimized. This will allow for an increased signal to noise ratio in the probes that contain them, resulting in more sensitive probes. In addition, the lack of a secondary fluorescence facilitates the use of additional fluorophores in multiplexed assay formats that utilize multiple distinct probes each containing a different fluorophore. If a quencher emitted light in a region, then additional probes could not bear fluorophores that emit light in that region.

New quenchers should also have physical properties that facilitate their purification and the purification of probes into which they are incorporated. They should also be chemically stable so that they can be incorporated into biological probes and used in assays without significant degradation. The quenchers should contain suitable reactive moieties to provide for their convenient incorporation into biologically relevant compounds such as lipids, nucleic acids, polypeptides, and more specifically antigens, steroids, vitamins, drugs, haptens, metabolites, toxins, environmental pollutants, amino acids, peptides, proteins, nucleotides, oligonucleotides, polynucleotides, carbohydrates, and the like. Lastly, the most useful compositions should be easily manufactured.

SUMMARY OF THE INVENTION

The invention provides non-fluorescing, fluorescence-quenching compositions, some of which have strong fluorescence quenching properties in the 520 nm range. Moreover, the quenchers of the present invention are chemically stable and can be easily manufactured and purified. The compositions can be incorporated into biologically relevant compounds and, in many cases, impart useful purification properties to these compounds. These and other advantages of the invention, as well as additional inventive features, will be apparent from the description of the invention provided herein.

The invention provides a novel group of azo quencher compositions that are useful as quenchers of fluorescence and to methods for making and using them. The quenchers of the invention contain an azo bond and 1,3,3-trimethyl-2-methyleneindoline ring system. The quenchers can be derivatized to facilitate their conjugation to a variety of biologically relevant compounds, including lipids, nucleic acids, peptides, proteins, and the like. The quenchers of this invention are termed dark quenchers because they release the energy they absorb from fluorophores without giving off light. The quenchers have the general formulas shown below in Formula 1 and Formula 2.

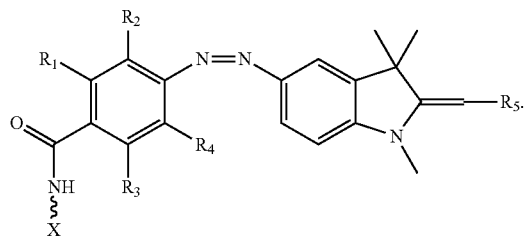

Formula 1

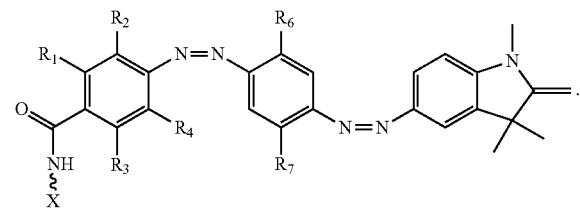

Formula 2

In another embodiment of the invention, compounds of the invention have the general formulas shown below in Formula 4, Formula 6, Formula 7, Formula 8, Formula 9 and Formula 10.

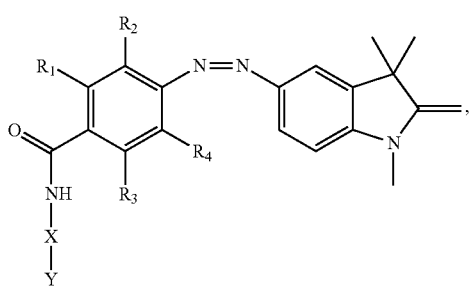

(Formula 4)

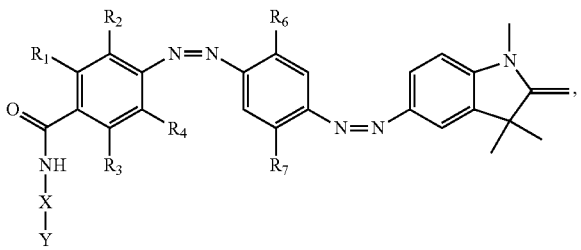

(Formula 6)

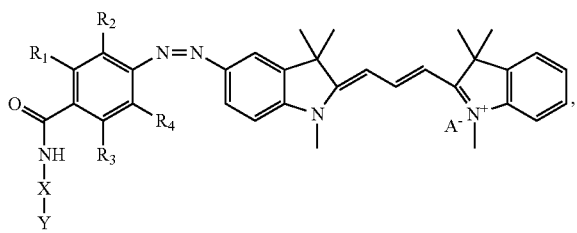

(Formula 7)

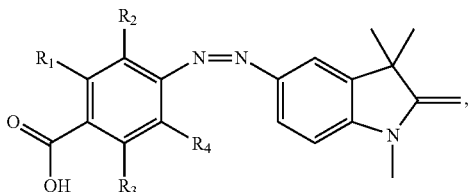

(Formula 8)

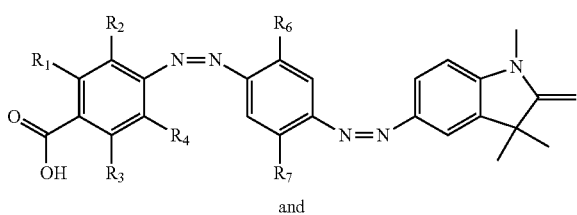

(Formula 9)

and

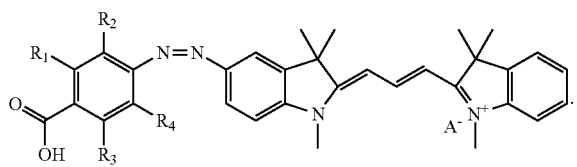

(Formula 10)

In Formulas 1, 2, 4, 6, 7, 8, 9 and 10 each of $R_1$, $R_2$, $R_3$ and $R_4$ is independently hydrogen, halogen, $NO_2$, $SO_3R$, $SO_2N(R)_2$, CN, CNS, keto, $(C_1-C_{10})$alkoxy, C1-C10 alkyl, aryl, or heteroaryl. Alternatively, either the $R_1/R_2$ pair or $R_3/R_4$, or both the $R_1/R_2$ pair and $R_3/R_4$ can be combined to form ring structures having five or six ring members, wherein these five or six-membered rings can be optionally substituted with halogen, $NO_2$, $SO_3R$, $SO_2N(R)_2$, CN, CNS, keto, $(C_1-C_{10})$ alkoxy, C1-C10 alkyl, aryl, or heteroaryl.

In Formulas $SO_3R$ and $SO_2N(R)_2$, R is H or C1-C10 alkyl.

In Formula 1, $R_5$ is arylalkenyl. "Arylalkenyl" means an aryl group that is attached to the conjugated ring system by a double bond to form a compound that is capable of quenching the fluorescence of a fluorophore. For example, one arylalkenyl represented by $R_5$ is:

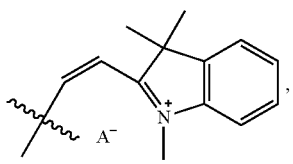

wherein A⁻ is an anion, for example, Cl⁻, Br⁻, I⁻, $ClO_4^-$, $BF_4^-$ or $CH_3COO^-$, and

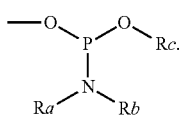

is the point of attachment of $R_5$.

In Formulas 2, 6 and 9, $R_6$ and $R_7$ is independently hydrogen, methyl or methoxy.

In Formulas 1, 2, 4, 6 and 7, X is a straight or branched aliphatic linker, having length of 1 to 100 C atoms optionally substituted with one or more heteroatoms selected from oxygen, nitrogen or sulfur, attached to a solid support that suitable for oligonucleotide synthesis. The quenchers can be derivatized to facilitate their conjugation to a variety of biologically relevant compounds, including lipids, nucleic acids, peptides, proteins, and the like. The invention also provides kits comprising, in one or more containers, at least one quencher dye composition of the present invention, and instructions for using that composition.

In Formulas 4, 6 and 7, Y is a controlled pore glass (CPG), polystyrene or

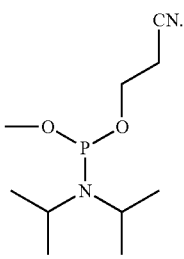

In a specific embodiment Y is

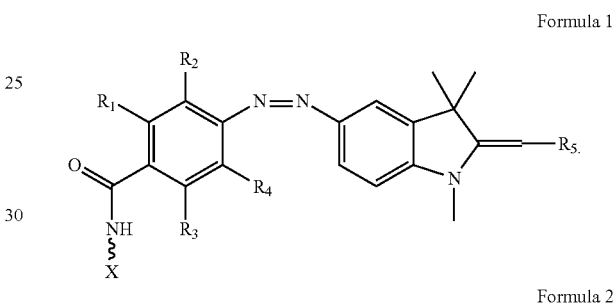

Each of $R_a$ and $R_b$ is straight or branched C1-C10 alkyl. $R_c$ is straight or branched C1-C10 alkyl or cyanoethyl.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
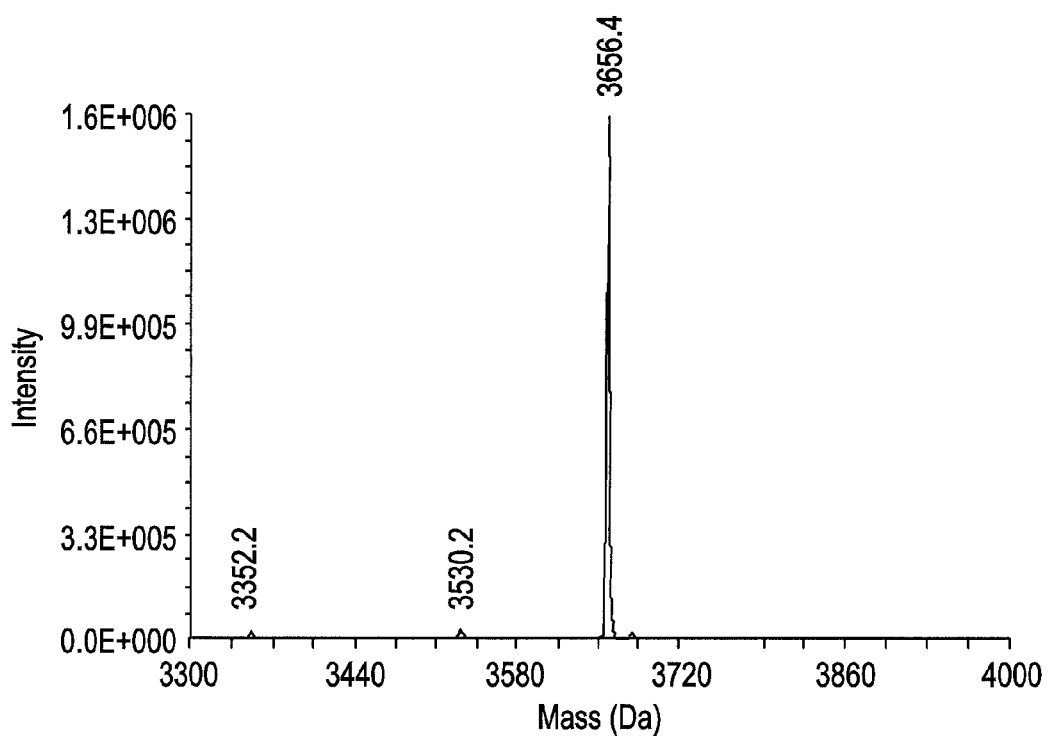
FIG. 1 is an ESI Mass spectrum of oligonucleotide SEQ ID NO 1.
Figure 2:
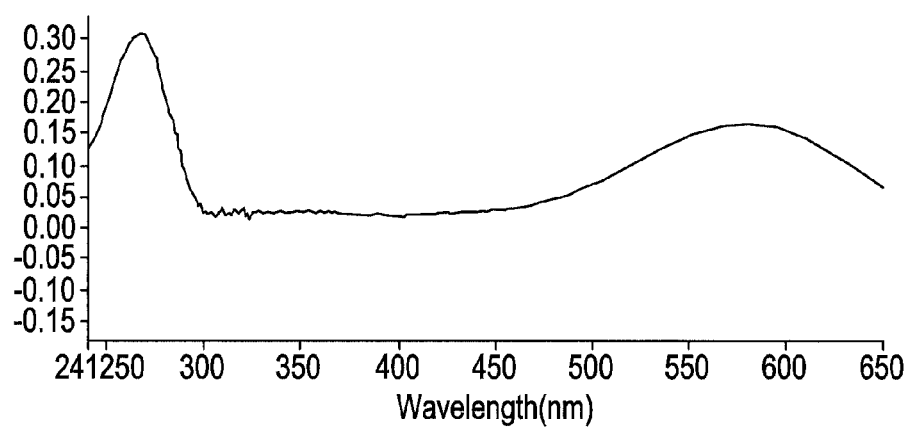
FIG. 2 is a UV/Vis Spectrum of oligonucleotide SEQ ID NO 1.
Figure 3:
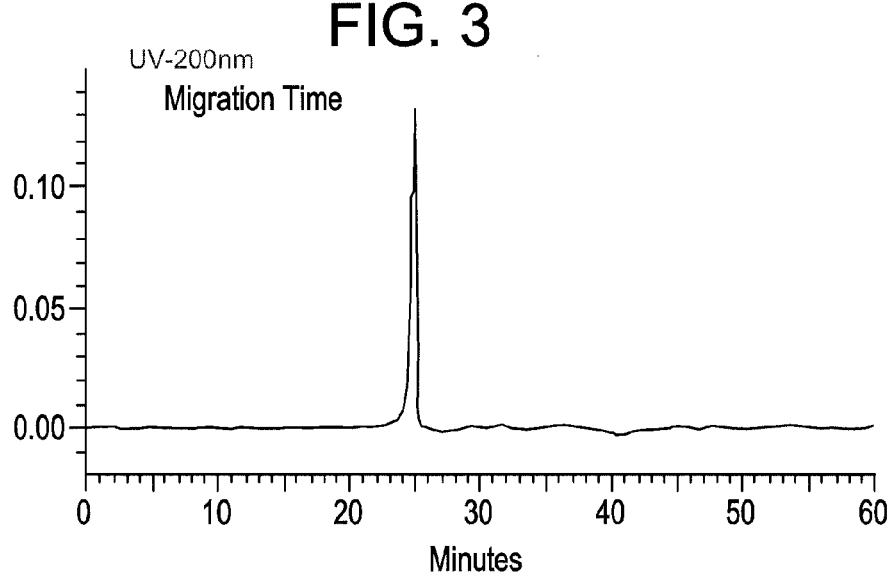
FIG. 3 is a CE Analysis of HPLC purified oligonucleotide SEQ ID NO 3.
Figure 4:
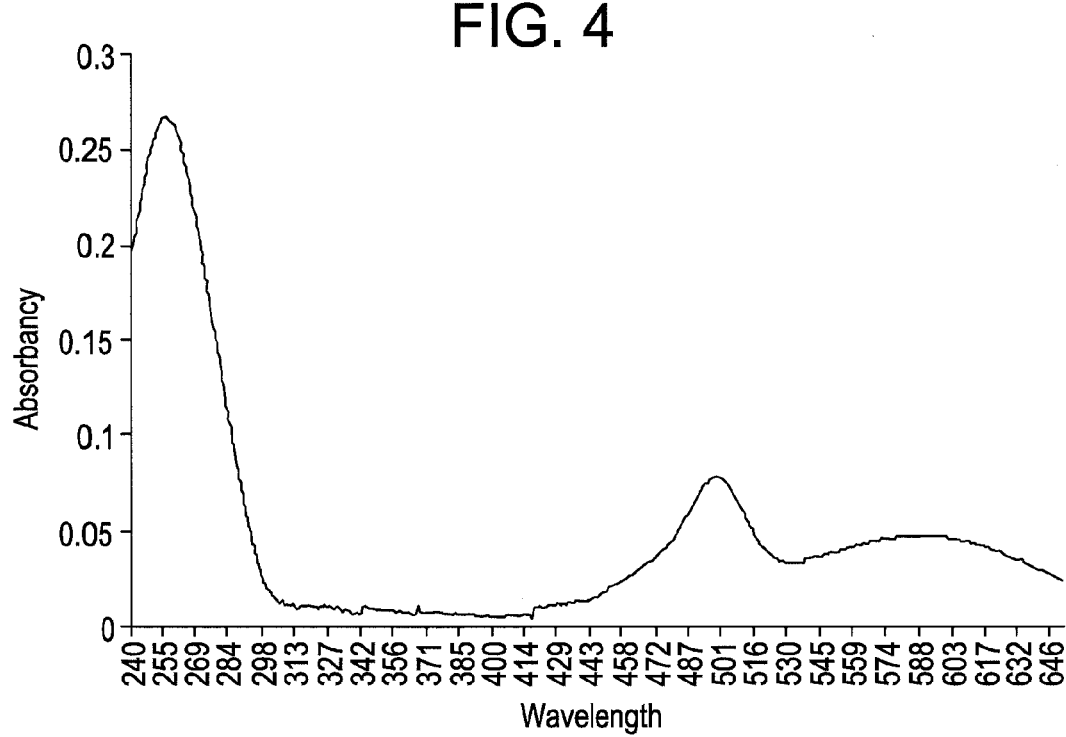
FIG. 4 is a UV/Vis Spectrum of oligonucleotide SEQ ID NO 3.

The invention provides a novel group of azo quencher compositions that are useful as quenchers of fluorescence and to methods for making and using them. The quenchers of this invention release the energy they absorb from fluorophores without giving off light. Consequently, they are called dark quenchers. The quenchers contain an azo bond and 1,3,3-trimethyl-2-methylene-indoline having the general formula shown below in Formula 1, Formula 2, and Formula 3.

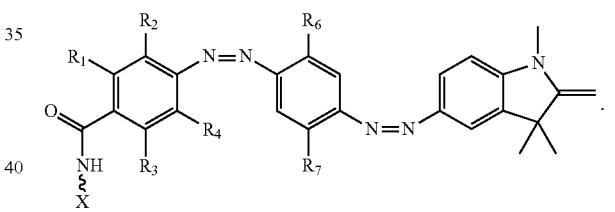

In Formula 1 and Formula 2, each of $R_1$, $R_2$, $R_3$ and $R_4$ is independently hydrogen, halogen, $NO_2$, $SO_3R$, $SO_2N(R)_2$, CN, CNS, keto, $(C_1-C_{10})$alkoxy, C1-C10 alkyl, aryl, or heteroaryl. Alternatively, either the $R_1/R_2$ pair or $R_3/R_4$, or both the $R_1/R_2$ pair and $R_3/R_4$ can be combined to form ring structures having five or six ring members, wherein these five or six-membered rings can be optionally substituted with halogen, $NO_2$, $SO_3R$, $SO_2N(R)_2$, CN, CNS, keto, $(C_1-C_{10})$alkoxy, C1-C10 alkyl, aryl, or heteroaryl.

In Formulas $SO_3R$ and $SO_2N(R)_2$, R is H or C1-C10 alkyl.

In certain embodiments one or more of $R_1$, $R_2$, $R_3$ and $R_4$ can further be selected from hydrogen.

In one embodiment, $R_6$ and $R_7$ are independently hydrogen, methyl or methoxy.

In Formula 1, X is a straight or branched aliphatic linker, having length of 1 to 100 C atoms optionally substituted with one or more heteroatoms selected from oxygen, nitrogen or sulfur, attached to a solid support, e.g. CPG or polystyrene.

In one embodiment $R_5$ is a hydrogen in Formula 1.

In another embodiment $R_5$ is arylalkenyl. "Arylalkenyl" means an aryl group that is attached to the conjugated ring system by a double bond to form a compound that is capable of quenching the fluorescence of a fluorophore. This structure is outlined in Formula 3, below.

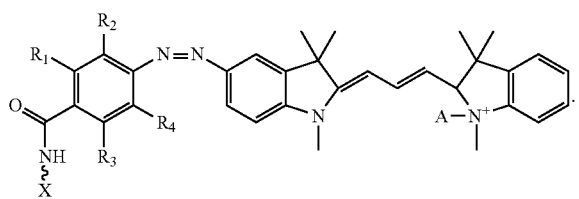

$A^-$ is an anion selected from $Cl^-$, $Br^-$, $I^-$, $ClO_4^-$, $BF_4^-$ or $CH_3COO^-$.

In one embodiment of the invention in Formulas 4, 6 and 7 Y is

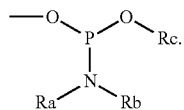

In another embodiment Y is

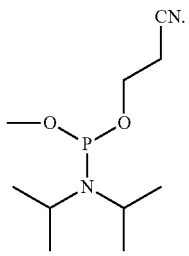

In one embodiment each of $R_a$ and $R_b$ is straight or branched C1-C10 alkyl.

In one embodiment of the invention $R_c$ is straight or branched C1-C10 alkyl or cyanoethyl.

The term "solid support" refers to any support that is compatible with oligonucleotide synthesis. For example, the following are suitable: glass, controlled pore glass (CPU), polymeric materials, polystyrene beads, coated glass, and the like.

"Alkyl" means straight chained or branched hydrocarbon. Typically, an alkyl group is $C_1$-$C_{10}$, more commonly $C_1$-$C_6$. Examples include methyl, ethyl, i-propyl, propyl, n-butyl, sec-butyl and tert-butyl.

"Aliphatic" means a straight or branched linear or cyclic hydrocarbon chain. Aliphatic groups may include diradicals such as alkylene, alkenylene, or alkynylene hydrocarbon chains. Carbon atoms within the aliphatic group may be substituted with heteroatoms such as oxygen, nitrogen or sulfur. For example, carbon atoms within a carbon chain could be substituted with oxygen atoms to form a polyethylene glycol chain.

Alkylene groups are diradicals and are saturated hydrocarbon chains without double or triple bonds, for example, —$CH_2CH_2CH_2$—. Alkenylene groups are diradicals and are unsaturated hydrocarbon chains that include at least one double bond, for example, —$CH=CH—CH_2$—. Alkynylene groups are diradicals and are unsaturated hydrocarbon chains that include at least one triple bond, for example, —$C\equiv C—CH_2$—. A hydrocarbon group may also include a double and triple bond simultaneously.

A "linker" is a diradical that attaches to two different groups. For example, —$CH_2CH_2CH_2$— is an aliphatic linker because it would attach to another moiety at both ends.

"Keto" means a compound of the structural formula $C(=O)C_1$-$C_{20}$ alkyl.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl.

The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents heteroaryl ring systems are as described above for aryl.

"Derivatized aromatic ring" means aminobenzoic acid optionally substituted with halogen, $NO_2$, $SO_3R$, $SO_2N(R)_2$, CN, CNS, keto, ($C_1$-$C_{10}$)alkoxy, C1-C10 alkyl, aryl, or heteroaryl. In one embodiment of the invention, the main compound ("derivatized aromatic ring") is not highly modified.

The invention also contemplates methods for preparing the disclosed compositions. The reaction between p-aminobenzoic acid and 1,3,3-trimethyl-2-methyleneindoline can be carried out by treating a suitable p-aminobenzoate with a suitable nitrite, such as $NaNO_2$, or a suitable organic nitrite in a suitable solvent and subsequently with $LiBF_4$ to create diazonium salt. The diazonium salt is then reacted with 1,3, 3-trimethyl-2-methyleneindoline, to generate an azo bonded ring system product. One method for carrying out this reaction sequence is described in more detail in Examples 1 and 3.

In another embodiment azo bonded ring system is conjugated with 2-(1,3,3-trimethylindolin-2-ylidene)acetaldehyde forming azo cyanine dye 4 (Scheme 1).

Scheme 1.

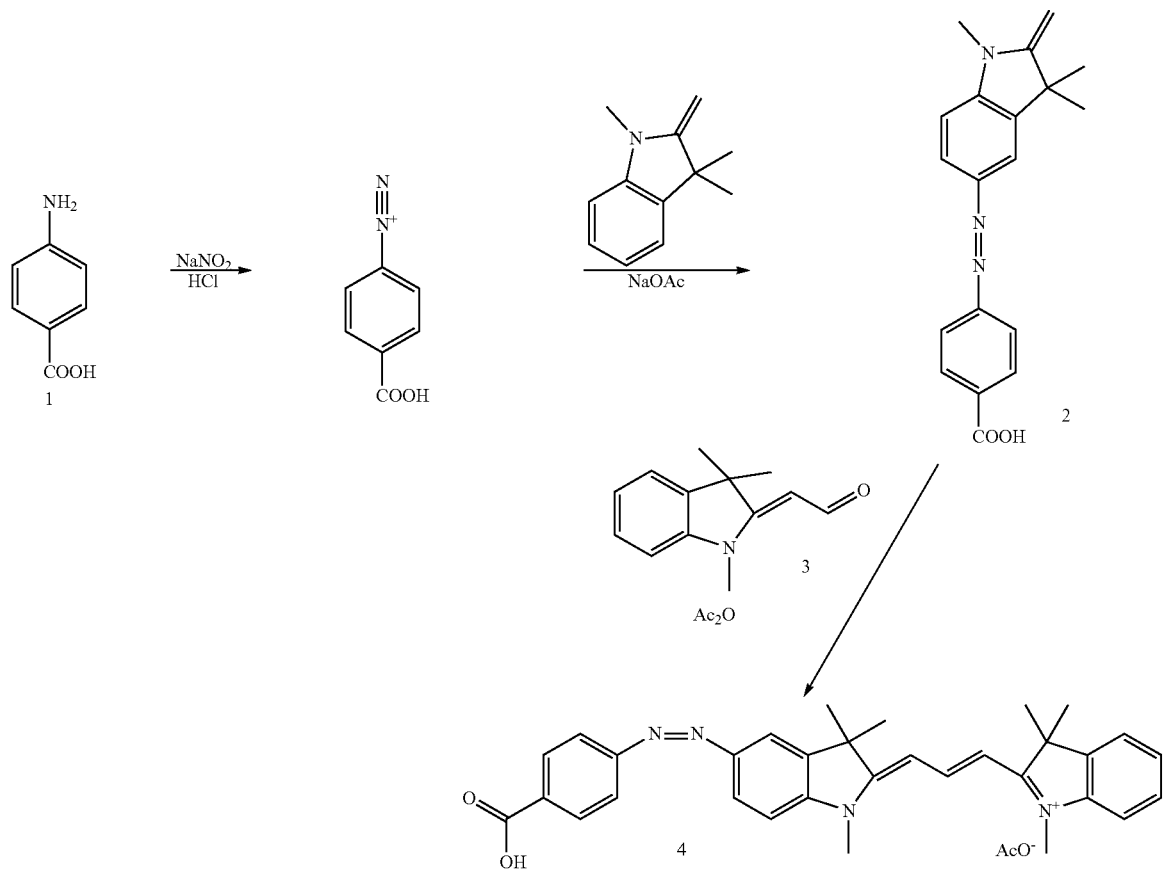

Once the azo product of Formula 1 is generated, it can be further modified to facilitate its use. For example, carboxyl group can be attached to linking groups or other molecules of interest. In one embodiment of Formula 1, X can be a straight or branched aliphatic linker, having length of 1 to 100 C atoms optionally substituted with one or more heteroatoms selected from oxygen, nitrogen or sulfur, attached to a solid support that has site chain protected with a trityl group described in Examples 4 and 5.

In another embodiment X is (C1-C100 alkyl)OH, preferably, (C1-C20 alkyl)OH, that can be converted into phosphoramidite building block suitable for reaction with a variety of nucleophiles, especially including hydroxyl groups by reaction with N,N-diisopropylamino cyanoethyl phosphonamidic chloride, as described in Example 3.

The phosphoramidite quenchers are ideally suited for incorporation into oligonucleotides. The support can serve as the foundation for oligonucleotide synthesis by standard methods. Although Examples 4 and 5 demonstrate the attachment of an azo-quencher compound to controlled pore glass, the method is more generally applicable to the attachment of the quencher to any solid support that contains a suitable number of free reactive nucleophilic groups, including polystyrene and polypropylene. The solid support-bound azo-quencher and trityl-protected, phosphoramidite quencher can both be used conveniently in conjunction with automated oligonucleotide synthesizers to directly incorporate the quencher into oligonucleotides during their chemical synthesis. In addition, the disclosed quenchers can be incorporated into oligonucleotides post synthetically. Such precursors and the oligonucleotides prepared with them are also contemplated by the present invention.

The disclosed quenching compositions can be linked to a variety of useful compounds other than oligonucleotides, provided that suitable reactive groups are present on those compounds. Such compounds include antigens, antibodies, steroids, vitamins, drugs, haptens, metabolites, toxins, environmental pollutants, amino acids, proteins, carbohydrates, lipids, and the like.

The invention also is directed to nucleic acid compositions containing dye pairs, which include one of the disclosed quencher compositions and a fluorescent dye that fluorescences on exposure to light of the appropriate wavelength. Suitable fluorescent dyes in the dye pair are those that emit fluorescence that can be quenched by the quencher of the dye pair. In certain embodiments, the dye pair can be attached to a single compound, such as an oligonucleotide. In other embodiments, the fluorescent reporter dye and the quencher can be on different molecules.

A wide variety of reactive fluorescent reporter dyes are known in the literature and can be used so long as they are quenched by the corresponding quencher dye of the invention. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluoroscein, rhodamine or other like compound. Suitable fluorescent reporters include xanthene dyes, such as fluorescein or rhodamine dyes, including 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); 1H,5H,11H, 15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16,17-octahydro-inner salt (TR or Texas Red); BODIPY™ dyes; benzoxaazoles; stilbenes; pyrenes; and the like. The fluorescent emission of certain reporter dyes is provided below.

| Fluorophore | Emission Max |
|---|---|
| Fluorescein | 520 nm |
| Tetrachloro fluorescein (TET) | 536 nm |
| Hexachlorofluorescein (HEX) | 556 nm |
| Cy3 | 570 nm |
| Tetramethylrhodamine (Tamra) | 580 nm |
| Cy3.5 | 596 nm |
| Carboxy-x-rhodamine (Rox) | 605 nm |
| Texas Red | 610 nm |
| Cy5 | 667 nm |
| Cy5.5 | 694 nm |

The quencher of Example 3 is capable of absorbing the fluorescent energy in the range of about 500 to about 660 nm and therefore can be used to quench the fluorescence of fluorescein through Cy5 (Table 1). The combination of azo bond with 1,3,3-trimethyl-2-methyleneindoline aromatic system makes them a very potent and useful fluorescence quenchers.

TABLE 1

Light absorbance properties of indoline azo chromophores 4, 6 and 9 in comparison with common commercially available fluorescence quenchers.

| Chromophore | $\lambda_{max}$, nm (solvent) | $\epsilon$, $M^{-1}$ $cm^{-1}$ |
|---|---|---|
| 6 | 490 (Buffer pH = 11) | 38,200 |
| 4 | 630 (Methanol) | 116,300 |
| 9 | 585 (Buffer pH = 11) | 48,500 |
| Dabcyl | 453 (Buffer pH = 11) | 32,000 |
| BHQ2 | 578 (Buffer pH = 11) | 38,000 |
| BlackBerry | 598 (Methanol) | 40,667 |

Many suitable forms of fluorescent reporter dyes are available and can be used depending on the circumstances. With xanthene compounds, substituents can be attached to xanthene rings for bonding with various reagents, such as for bonding to oligonucleotides. For fluorescein and rhodamine dyes, appropriate linking methodologies for attachment to oligonucleotides have also been described. See for example, Khanna et al. U.S. Pat. No. 4,439,356; Marshall (1975) Histochemical J., 7:299-303; Menchen et al., U.S. Pat. No. 5,188, 934; Menchen et al., European Patent Application No. 87310256.0; and Bergot et al., International Application PCT/US90/05565).

Preferably, when the dye pair is in a configuration in which the reporter dye is effectively quenched by the quencher dye, its fluorescence is reduced by at least a factor of 80%, and more preferably by 90%, 95%, or 98%, when compared to its fluorescence in the absence of quenching. Compositions with 99%, 99.5%, 99.9% and higher levels of quenching have also been prepared with the quencher of Example 4. High levels of quenching allow for the preparation of oligonucleotide probes having a high signal to noise ratio which is defined as the amount of signal present when the composition is in its maximal unquenched state (signal) versus its maximally quenched state (noise).

Probes having a high signal to noise ratio are desirable for the development of highly sensitive assays. To measure signal to noise ratios relative fluorescence is measured in a configuration where the quencher and fluorophore are within the Förster distance and the fluorophore is maximally quenched (background fluorescence or "noise") and compared with the fluorescence measured when fluorophore and quencher are separated in the absence of quenching ("signal"). The signal to noise ratio of a dye pair of the invention will generally be at least about 2:1 but generally is higher. Signal to noise ratios of about 5:1, 10:1, 20:1, 40:1 and 50:1 are preferred. Ratios of 60:1, 70:1 and even up to 100:1 and higher can also be obtained in some cases. Intermediate signal to noise ratios are also contemplated.

Suitable dye-pairs can be used in many configurations. For example, the dye pair can be placed on nucleic acid oligomers and polymers. In this format, a dye-pair can be placed on an oligomer having a hairpin structure such that the fluorophore and quencher are within the Förster distance and FRET occurs.

In other embodiments, dye pairs can be placed on an oligomer that can adopt a random coil conformation, such that fluorescence is quenched until the oligonucleotide adopts an extended conformation, as when it becomes part of a duplex nucleic acid polymer. In general, the individual dye moieties can be placed at any position of the nucleic acid depending upon the requirements of use.

Nucleic acid oligomers and polymers that include the dye pairs of the invention can be used to detect target nucleic acids. In one method, the individual components of a dye-pair can be on opposing, annealable, self-complementary segments of a single oligonucleotide such that when the oligonucleotide anneals to itself in the absence of exogenous sequences, FRET occurs. The oligonucleotide is constructed in such a way that the internal annealing is disrupted and fluorescence can be observed when it hybridizes to nucleic acid polymers having sufficient complementarity. Such an oligonucleotide can be used to rapidly detect nucleic acid polymers having sequences that bind to the oligonucleotide. In another embodiment, such a composition comprises two biomolecules, such as oligonucleotides, one of which is attached to a reporter dye and the other of which is attached as a quencher dye.

Oligonucleotide probes lacking self-complementarity can also be utilized in a similar manner. For example, a quencher and fluorophore can be placed on an oligonucleotide that lacks the self-annealing property such that the random-coil conformation of the oligonucleotide keeps the fluorophore and quencher within a suitable distance for fluorescence quenching. Such oligonucleotides can be designed so that when they anneal to desired target nucleic acid polymers the fluorophore and quencher are more separated and the spectral characteristics of the fluorophore become more apparent.

Other DNA binding formats are also possible. For example, two oligonucleotides can be designed such that they can anneal adjacent to each other on a contiguous length of a nucleic acid polymer. The two probes can be designed such that when they are annealed to such a nucleic acid polymer a quencher on one of the oligonucleotides is within a sufficient proximity to a fluorophore on the other oligonucleotide for FRET to occur. Binding of the oligonucleotides to the nucleic acid polymer can be followed as a decrease in the fluorescence of the fluorophore.

Alternatively, a set of oligonucleotides that anneal to each other can be configured such that a quencher and a fluorophore are positioned within the Förster distance on opposing oligonucleotides. Incubation of such an oligonucleotide duplex with a nucleic acid polymer that competes for binding of one or both of the oligonucleotides would cause a net separation of the oligonucleotide duplex leading to an increase in the fluorescent signal of the reporter dye. To favor binding to the polymer strands, one of the oligonucleotides could be longer or mismatches could be incorporated within the oligonucleotide duplex.

These assay formats can easily be extended to multi-reporter systems that have mixtures of oligonucleotides in which each oligonucleotide has a fluorophore with a distinct spectrally resolvable emission spectrum. The binding of individual oligonucleotides can then be detected by determining the fluorescent wavelengths that are emitted from a sample. Such multi-reporter systems can be used to analyze multiple hybridization events in a single assay.

Oligonucleotides can also be configured with the disclosed quenchers such that they can be used to monitor the progress of PCR reactions without manipulating the PCR reaction mixture (i.e., in a closed tube format). The assay utilizes an oligonucleotide that is labeled with a fluorophore and a quencher in a configuration such that fluorescence is substantially quenched. The oligonucleotide is designed to have sufficient complementarity to a region of the amplified nucleic acid so that it will specifically hybridize to the amplified product. The hybridized oligonucleotide is degraded by the exonuclease activity of Taq polymerase in the subsequent round of DNA synthesis. The oligonucleotide is designed such that as the oligomer is degraded, one of the members of the dye-pair is released and fluorescence from the fluorophore can be observed. An increase in fluorescence intensity of the sample indicates the accumulation of amplified product.

The invention also provides kits that include in one or more containers, at least one of the disclosed quenching dye compositions and instructions for its use. In one embodiment, the kits of the invention comprise oligonucleotide sequences SEQ ID 3 and SEQ ID 4. Such kits can be useful for practicing the described methods or to provide materials for synthesis of the compositions as described. Additional components can be included in the kit depending on the needs of a particular method. For example, where the kit is directed to measuring the progress of PCR reactions, it can include a DNA polymerase.

The following examples further illustrate the invention but, of course, should not be construed as in any way limiting its scope. In particular the following examples demonstrate synthetic methods for obtaining the compounds of the invention. Starting materials useful for preparing the compounds of the invention and intermediates thereof, are commercially available or can be prepared from commercially available materials using known synthetic methods and reagents. All oligonucleotide sequences are written from the 5'-terminus on the left to the 3'-terminus on the right.

EXPERIMENTAL

Examples

Example 1

Synthesis of 5-(2-nitro-4-carboxyphenylazo)-1,3,3-trimethyl-2-methyleneindoline (6). To a cold solution of 10 g (54.9 mmol) of 2-nitro-4-aminobezoic acid (5) and 2.4 g (22.6 mmol) of sodium carbonate in 100 mL of DI water was added a solution of 3.5 g (50.7 mmol) of $NaNO_2$ in 10 mL of DI water at 15° C. with stirring. The above mixture was poured into a mixture of 10 mL of concentrated HCl and 60 gm of crashed ice with stirring. Then of 9.5 g (54.9 mmol) of 1,3,3-trimethyl-2-methyleneindoline and 6 ml of acetic acid were added to the reaction mixture. After 10 min the reaction mixture was neutralized with 8 mL of 20% NaOH solution in water. The precipitant was filtered. Flash chromatography with chloroform/hexanes/acetone 5:3:2 mobile system provided 7 g (34.7%) of azo bezoate (6) as orange solid. TLC $R_f$ 0.23 (chloroform/hexanes/acetone 5:3:2). UV/Vis (buffer pH=11) $\lambda_{max}$ (nm) 490 ($\epsilon$=38,200 $M^{-1}cm^{-1}$). ESIMS 367.6 [$C_{19}H_{18}N_4O_4$ (M+H)$^+$ requires 367.4].

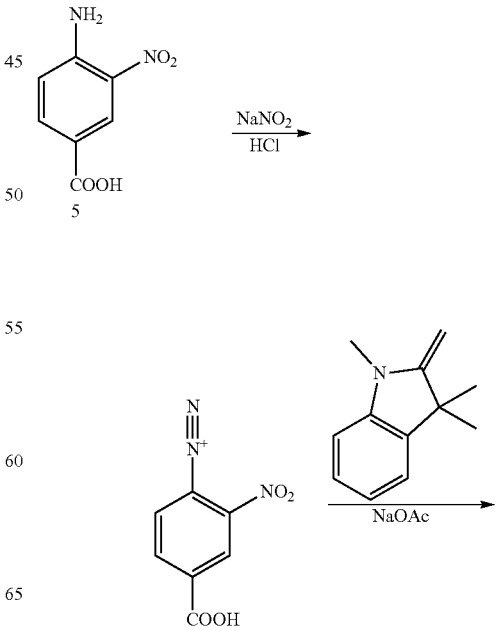

Scheme 2.

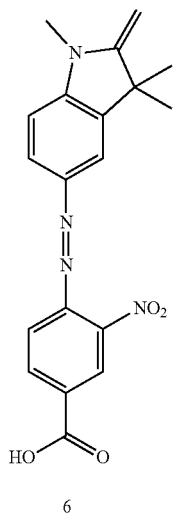

Synthesis of 2-(5-(5-(4-carboxyphenylazo)-1,3,3-trimethyl-2-yliden)prop-1-enyl)-1,3,3-trimethyl-3H-indolium acetate (4). The synthesis was as shown in Scheme 1.

5-(4-carboxyphenylazo)-1,3,3-trimethyl-2-methyleneindoline (2). To a cold solution of 10 g (72.9 mmol) of p-aminobezoic acid and 2.4 g (22.6 mmol) of sodium carbonate in 100 mL of DI water was added a solution of 3.5 g (50.7 mmol) of NaNO$_2$ in 10 mL of DI water at 15° C. with stirring. The above mixture was poured into a mixture of 10 mL of concentrated HCl and 60 gm of crashed ice with stirring. Then of 10.8 g (62.4 mmol) of 1,3,3-trimethyl-2-methyleneindoline and 6 ml of acetic acid were added to the reaction mixture. After 10 min the reaction mixture was neutralized with 8 mL of 20% NaOH solution in water. The precipitant was filtered. Flash chromatography with chloroform/hexanes/acetone 5:3:2 mobile system provided 7.3 g (31.1%) of azo bezoate (2) as orange solid. TLC R$_f$ 0.26 (chloroform/hexanes/acetone 5:3:2). UV/Vis (methanol) λ$_{max}$ (nm) 455 (ε=32,600 M$^{-1}$cm$^{-1}$). ESMS 322.3 [C$_{19}$H$_{19}$N$_3$O$_2$ (M+H)$^+$ requires 322.4].

2-(5-(5-(4-carboxyphenylazo)-1,3,3-trimethyl-2-yliden)prop-1-enyl)-1,3,3-trimethyl-3H-indolium acetate (4). 5 g (15.6 mmol) of 5-(4-carboxyphenyl-azo)-1,3,3-trimethyl-2-methyleneindoline (2) and 3.1 g (15.4 mmol) of 2-(1,3,3-trimethylindolin-2-ylidene)acetaldehyde were heated in 50 mL of acetic anhydride at 105° C. for 1 h. After cooling to room temperature, acetic anhydride was removed under reduced pressure and the residue was applied to a silica gel column; elution with a gradient of 0:1-1:19 MeOH-DCM provided cyanine (4) as dark blue solid. Yield: 500 mg (5.6%); TLC R$_f$ 0.48 (1:9 MeOH-DCM). UV/Vis (methanol) λ$_{max}$ (nm) 630 (ε=116,300 ESIMS 567.9 [C$_{34}$H$_{36}$N$_4$O$_4$ (M+H)$^+$ requires 565.7].

Example 3

Synthesis of 5-(4-(4-carboxamidophenylazo)-2,5-dimethoxyphenylazo)-1,3,3-trimethyl-2-methyleneindoline phosphoramidite (11). The synthesis was as shown in Scheme 3 below.

4-(4-carboxyphenylazo)-2,5-dimethoxyaniline (8). To a cold solution of 10 g (72.9 mmol) of p-aminobezoic acid (3) and 2.4 g (22.6 mmol) of sodium carbonate in 100 mL of DI water was added a solution of 3.5 g (50.7 mmol) of NaNO$_2$ in 10 mL of DI water at 15° C. with stirring. The above mixture was poured into a mixture of 10 mL of concentrated HCl and 60 gm of crashed ice with stirring. Then of 11.2 g (73.2 mmol) of dimethoxyaniline (7) and 6 ml of acetic acid were added to the reaction mixture. After 10 min the reaction mixture was neutralized with 8 mL of 20% NaOH solution in water. The precipitant was filtered. Flash chromatography with chloroform/hexanes/acetone 5:3:2 mobile system provided 16 g (72.7%) of azo bezoate (8) as orange solid. TLC R$_f$ 0.33 (1:9 MeOH-DCM). UV/Vis (methanol) λ$_{max}$ (nm) 450 (ε=31,800 M$^{-1}$cm$^{-1}$). $^1$H NMR (DMSO/D$_2$O) δ 3.76 (s, 3H), 3.84 (s, 3H), 6.45 (s, 1H), 7.25 (s, 1H), 7.69 (d, 2H, J=8.4 Hz), 8.00 (d, 2H, J=8.4 Hz). ESMS 302.3 [C$_{15}$H$_{15}$N$_3$O$_4$ (M+H)$^+$ requires 302.3].

5-(4-(4-carboxyphenylazo)-2,5-dimethoxyphenylazo)-1,3,3-trimethyl-2-methyleneindoline (9). To a cold solution of 5 g (16.6 mmol) of 4-(4-carboxy-phenylazo)-2,5-dimethoxyaniline (8) and 1.25 g (11.8 mmol) of sodium carbonate in 50 mL of DI water was added a solution of 1.75 g (25.4 mmol) of NaNO$_2$ in 5 mL of DI water at 15° C. with stirring. The above mixture was poured into a mixture of 5 mL of concentrated HCl and 30 gm of crashed ice with stirring. Then of 2.9 g (16.6 mmol) of 1,3,3-trimethyl-2-methyleneindoline and 1.5 ml of acetic acid were added to the reaction mixture. After 10 min the reaction mixture was neutralized with 6 mL of 20% NaOH solution in water. The precipitant was filtered. Flash chromatography with chloroform/hexanes/acetone 5:3:2 mobile system provided 5.5 g (68.2%) of azo bezoate (9) as dark blue solid. TLC R$_f$ 0.48 (1:9 MeOH-DCM). UV/Vis (buffer pH=11) λ$_{max}$ (nm) 585 (ε=48,500 M$^{-1}$cm$^{-1}$). 486.6 [C$_{27}$H$_{27}$N$_5$O$_4$ (M+H)$^+$ requires 486.5].

Azo alcohol 10. To the solution of 200 mg (0.41 mmol) of 5-(4-(4-carboxyphenylazo)-2,5-dimethoxyphenylazo)-1,3,3-trimethyl-2-methyleneindoline (8) and 83.4 μL (0.49 mmol) of DIPEA in 0.6 mL of acetonitrile were added 187.4 mg (0.49 mmol) of HBTU followed by addition of 72.5 mg (0.62 mmol) of 6-aminohexanol with stirring at room temperature. After 12 hrs the reaction mixture was diluted with 3 mL of chloroform and washed with 5 mL of brine. The organic layer was separated and dried over anhydrous Na$_2$SO$_4$. Flash chromatography with 92:8 chloroform/methanol mobile system provided 205.0 mg (85.1%) of 10. TLC R$_f$ 0.50 (8:92 MeOH-DCM). ESMS 585.8 [C$_{33}$H$_{40}$N$_6$O$_4$ (M+H)$^+$ requires 585.8].

5-(4-(4-carboxamidophenylazo)-2,5-dimethoxyphenylazo)-1,3,3-trimethyl-2-methyleneindoline phosphoramidite 11. To the solution of 205.0 mg (0.35 mmol) of the compound 10, 152.64 (0.88 mmol) of DIPEA in 1.6 mL of THF were added 86.1 μL (0.39 mmol) of 2-cyanoethyl-N,N, diisopropylphosphonamidic chloride dropwise with stirring under Ar at room temperature. After 1.25 hrs the reaction mixture was diluted with 20 mL of ethylacetate and washed with 50 mL of saturated sodium bicarbonate and 50 mL of brine. The organic layer was separated and dried over 5 g of anhydrous Na$_2$SO$_4$. Flash chromatography with 5:4:1 ethylacetate/hexanes/triethylamine mobile system provided 110 mg (40.0%) of the compound 11. TLC R$_f$ 0.15 (5:4:1 ethylacetate/hexanes/triethylamine). $^{31}$P NMR (CDCl$_3$) δ 148.9. ESMS 784.9 [C$_{42}$H$_{57}$N$_8$O$_5$P (M+H)$^+$ requires 784.9].

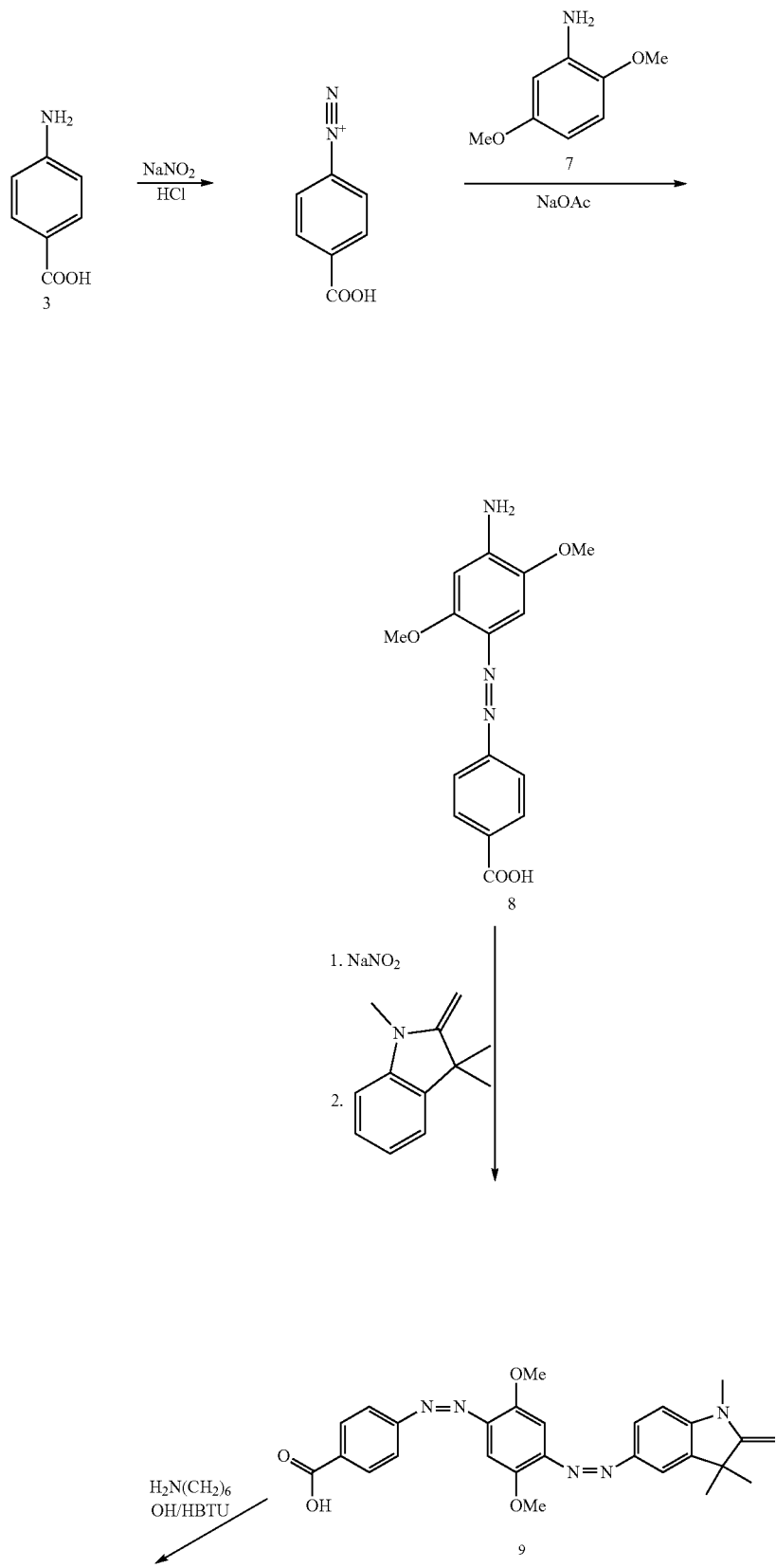
Scheme 3.

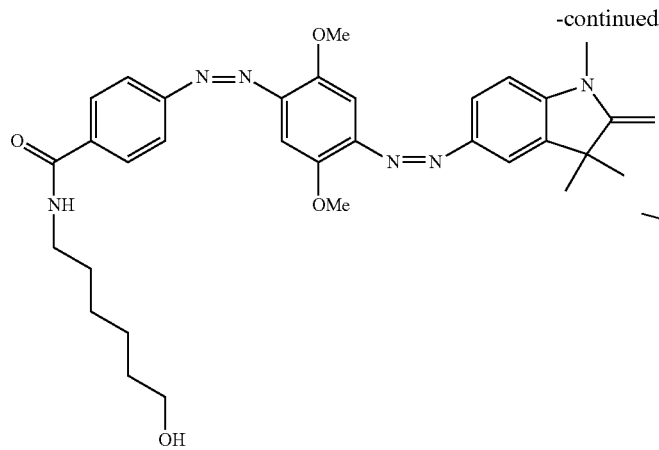

10

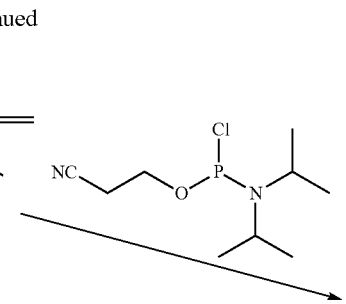

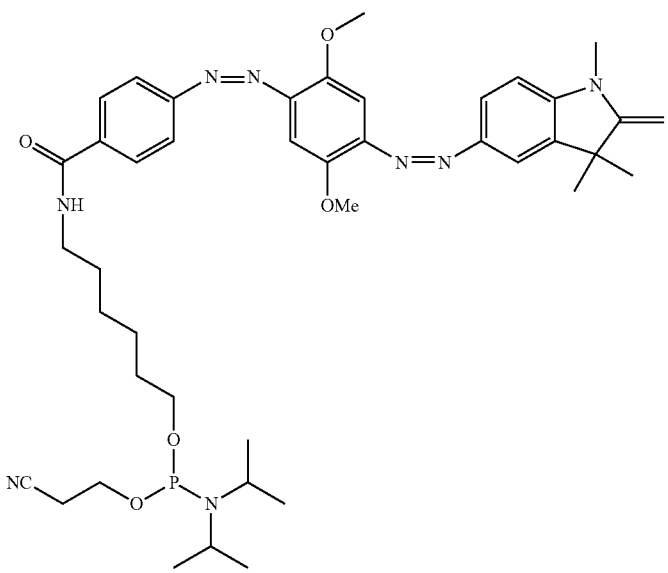

11

Example 4

Synthesis of 5-(4-(4-carboxamidophenylazo)-2,5-dimethoxyphenylazo)-1,3,3-trimethyl-2-methyleneindoline derivatized CPG (14). The synthesis was as shown in Scheme 4 below.

DMT Protected azo alcohol 13. To the solution of 500 mg (1.03 mmol) of 5-(4-(4-carboxyphenylazo)-2,5-dimethoxyphenylazo)-1,3,3-trimethyl-2-methyleneindoline (9) and 177 mg (1.55 mmol) of N-hydroxy succinimide in 5 mL of DMF were added 233 mg (1.13 mmol) of DCC at room temperature under nitrogen with stirring. After 12 hrs the reaction mixture was filtered and 599 mg (1.33 mmol) of alcohol 12 were added to the reaction mixture at room temperature with stirring. After 12 hrs the reaction mixture was diluted with 50 mL of chloroform and washed with 30 mL of brine. The organic layer was separated and dried over anhydrous $Na_2SO_4$. Flash chromatography with Flash chromatography with 5:4:1 ethylacetate/hexanes/triethylamine mobile system provided 750 mg (79.3%) of the compound 13. TLC $R_f$ 0.48 (8:92 MeOH-DCM). UV/Vis (methanol) $\lambda_{max}$ (nm) 560 ($\epsilon$=45,900 $M^{-1}cm^{-1}$). ESMS 920.0 [$C_{55}H_{60}N_6O_7$ $(M+H)^+$ requires 919.1].

Succinate 14. To the solution of 750 mg (0.82 mmol) of the compound 13 and 20 mg (1.64 mmol) of DMAP in 7.5 mL of pyridine were added 163.8 mg (1.64 mmol) of succinic anhydride with stirring at 37° C. After 12 hrs the reaction mixture was diluted with 50 mL of chloroform and washed with 50 mL of brine. The organic layer was separated and dried over anhydrous $Na_2SO_4$. Flash chromatography with 9:1 chloroform/methanol provided 750 mg (91.8%) of 14. TLC $R_f$ 0.33 (1:9 MeOH-DCM). ESMS 1018.2 [$C_{59}H_{64}N_6O_{10}$ $(M+H)^+$ requires 1018.2].

5-(4-(4-Carboxamidophenylazo)-2,5-dimethoxyphenylazo)-1,3,3-trimethyl-2-methyleneindoline derivatized CPG (15). To the suspension of 10 g of amino-lcca-CPG, 102 µL of DIPEA and 750 mg (0.75 mmol) of succinate 14 in 25 mL of acetonitrile were added 307 mg (0.83 mmol) of HBTU at room temperature. After 12 hrs CPG was filtered, washed with 3×20 mL portions of acetonitrile, capped with acetic anhydride in pyridine/N-methylimidazole mixture and washed 3×20 mL portions of acetonitrile. The solid support was dried under diminished pressure and nucleoside loading was measured by DMT removal procedure yielding 10 g of final product with 27.4 µmol/g loading.

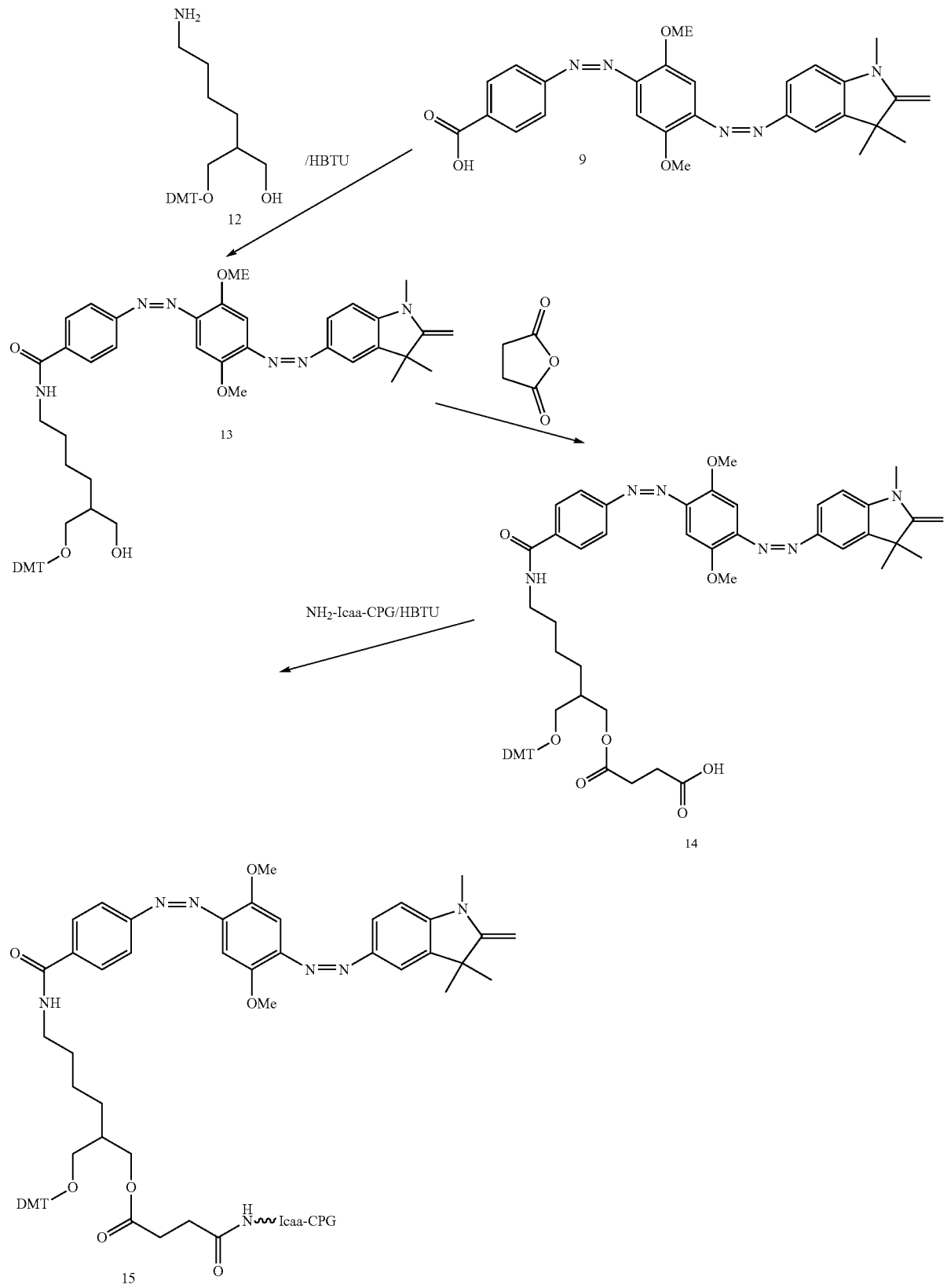

Example 5

Synthesis of 5-(2-nitro-4-carboxyphenylazo)-1,3,3-trimethyl-2-methyleneindoline derivatized CPG 18. The synthesis was as shown in Scheme 5 below.

DMT Protected azo alcohol 16. To the solution of 1 g (2.7 mmol) of 5-(2-nitro-4-carboxyphenylazo)-1,3,3-trimethyl-2-methyleneindoline (6) and 471 mg (4.1 mmol) of N-hydroxy succinimide in 10 mL of DMF were added 619 mg (3.0 mmol) of DCC at room temperature under nitrogen with stirring. After 12 hrs the reaction mixture was filtered and 2.4 g (5.4 mmol) of alcohol 12 were added to the reaction mixture at room temperature with stirring. After 12 hrs the reaction mixture was diluted with 50 mL of chloroform and washed with 30 mL of brine. The organic layer was separated and dried over anhydrous $Na_2SO_4$. Flash chromatography with Flash chromatography with 5:4:1 ethylacetate/hexanes/triethylamine mobile system provided 780 mg (36.2%) of the compound 16. TLC $R_f$ 0.48 (8:92 MeOH-DCM). ESMS 798.8 [$C_{47}H_{51}N_5O_7$ (M+H)$^+$ requires 798.4].

Succinate 17. To the solution of 120.0 mg (0.15 mmol) of the compound 16 and 3.7 mg (0.03 mmol) of DMAP in 1.2 mL of pyridine were added 30.1 mg (0.3 mmol) of succinic anhydride with stirring at 37° C. After 12 hrs the reaction mixture was diluted with 3 mL of chloroform and washed with 5 mL of brine. The organic layer was separated and dried over anhydrous $Na_2SO_4$. Flash chromatography with 19:1 chloroform/methanol provided 100 mg (74.0%) of 17. TLC $R_f$ 0.45 (1:19 MeOH-DCM). ESMS 899.1 [$C_{51}H_{55}N_5O_{10}$ (M+H)$^+$ requires 899.0].

5-(4-(4-Carboxamidophenylazo)-2,5-dimethoxyphenylazo)-1,3,3-trimethyl-2-methyleneindoline derivatized CPG 18. To the suspension of 1 g of amino-lcca-CPG, 17.3 μL of DIPEA and 100 mg (0.11 mmol) of succinate 17 in 300 μL of acetonitrile were added 46.4 mg (0.12 mmol) of HBTU at room temperature. After 12 hrs CPG was filtered, washed with 3×20 mL portions of acetonitrile, capped with acetic anhydride in pyridine/N-methylimidazole mixture and washed 3×20 mL portions of acetonitrile. The solid support was dried under diminished pressure and nucleoside loading was measured by DMT removal procedure yielding 18 g of final product with 39.8 μmol/g loading.

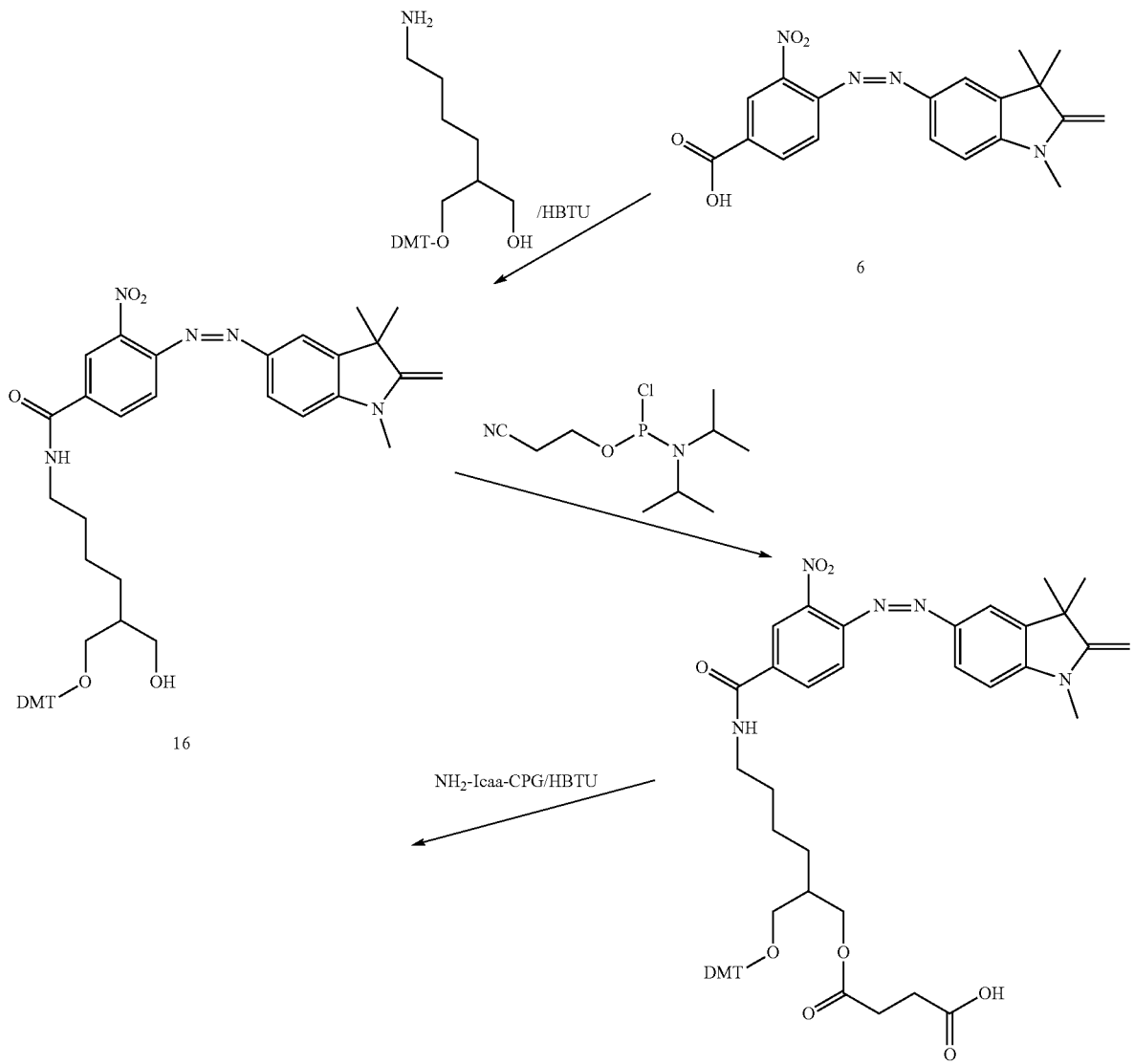

Scheme 5.

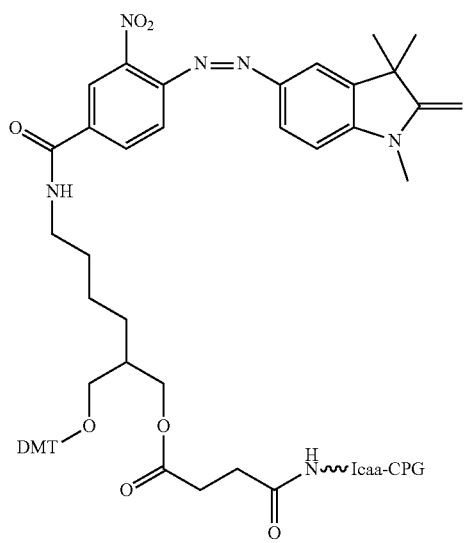

18

Example 6

Oligonucleotide Synthesis: The following oligonucleotides (Table 2) were synthesized using 3'→5' directed standard phosphoramidite chemistry in 1 μmole scale. The syntheses were performed on Expedite 8900 synthesizer using standard DNA 1 μmole cycles.

Following synthesis, the controlled pore glass (CPG) solid support was transferred to a 2 ml microfuge tube. Oligonucleotides were cleaved from the CPG and deprotected by incubation for 6 hrs at 65° C. in 1 ml of concentrated ammonia (~28-30%) solution in water. The supernatant was removed and the CPG was washed with 1 ml of water; supernatants were pooled and dried.

TABLE 2

3'-Modified oligonucleotide sequences.

SEQ ID NO 1   TTTTTTTTTT(9)

SEQ ID NO 2   TTTTTTTTTT(6)

TABLE 2-continued

3'-Modified oligonucleotide sequences.

SEQ ID NO 3   (Fam)TGCCATCCTGGATTCCAGAAGATTCAAC(9)

SEQ ID NO 4   (Fam)AGGAAAACAGCCACCAGGTGAAGGAGG(9)

Crude oligonucleotides were analyzed by CE and the identities of the oligonucleotides SEQ ID NO 1-4 were confirmed by ESI mass-spectrometry.

While this invention has been particularly shown and described with references to example embodiments thereof, it will be understood by those skilled in the art that various changes in form and details may be made therein without departing from the scope of the invention encompassed by the appended claims.

We claim:

1. A compound represented by Formula 4:

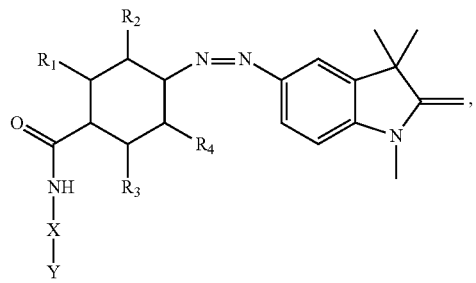

(Formula 4)

wherein:
each of $R_1$, $R_2$, $R_3$ and $R_4$ is independently hydrogen, halogen, $NO_2$, $SO_3R$, $SO_2N(R)_2$, CN, CNS, ($C_1$-$C_{10}$) alkoxy, $C_1$-$C_{10}$ alkyl, aryl, or heteroaryl; or $R_1$ and $R_2$ together or $R_3$ and $R_4$ together form a five- or six-membered ring, wherein said five- or six-membered ring is optionally substituted with halogen, $NO_2$, $SO_3R$, $SO_2N(R)_2$, CN, CNS, keto, ($C_1$-$C_{10}$)alkoxy, $C_1$-$C_{10}$ alkyl, aryl, or heteroaryl;

R is H or $C_1$-$C_{10}$ alkyl;

X is a $C_1$-$C_{100}$ straight or branched alkyl linking group, wherein one or more carbon atoms is optionally replaced with a nitrogen, oxygen or sulfur atom, or a combination thereof; and Y is controlled pore glass (CPG), polystyrene or

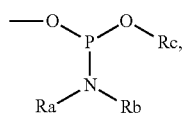

wherein each of $R_a$ and $R_b$ is straight or branched $C_1$-$C_{10}$ alkyl; and $R_c$ is straight or branched $C_1$-$C_{10}$ alkyl or cyanoethyl.

2. The compound of claim 1, wherein:

X is a $C_1$-$C_{100}$ straight or branched alkyl linking group, wherein one or more carbon atoms are optionally replaced with nitrogen, oxygen or sulfur, or a combination thereof; and Y is controlled pore glass (CPG) or polystyrene.

3. The compound of claim 1, wherein:

X is a $C_1$-$C_{100}$ straight or branched alkyl linking group, wherein one or more carbon atoms are optionally replaced with nitrogen, oxygen or sulfur, or a combination thereof; and Y is

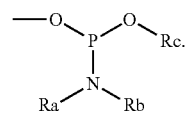

4. A compound represented by formula 6:

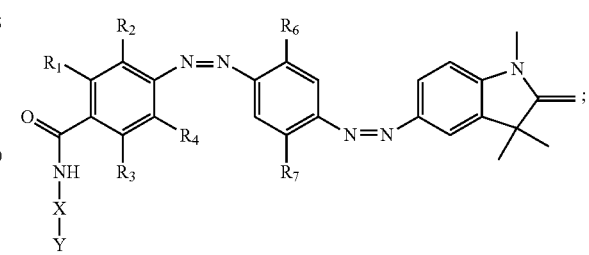

Formula 6 wherein:
each of $R_1$, $R_2$, $R_3$ and $R_4$ is independently hydrogen, halogen, $NO_2$, $SO_3R$, $SO_2N(R)_2$, CN, CNS, ($C_1$-$C_{10}$) alkoxy, $C_1$-$C_{10}$ alkyl, aryl, or heteroaryl; or $R_1$ and $R_2$ together or $R_3$ and $R_4$ together form a five- or six-membered ring, wherein said five- or six-membered ring is optionally substituted with halogen, $NO_2$, $SO_3R$, $SO_2N(R)_2$, CN, CNS, ($C_1$-$C_{10}$)alkoxy, $C_1$-$C_{10}$ alkyl, aryl, or heteroaryl;

R is H or $C_1$-$C_{10}$ alkyl;

each of $R_6$ and $R_7$ is independently hydrogen, methyl, or methoxy;

X is a $C_1$-$C_{100}$ straight or branched alkyl linking group, wherein one or more carbon atoms are optionally replaced with nitrogen, oxygen or sulfur, or a combination thereof; and Y is controlled pore glass (CPG), polystyrene or

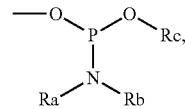

wherein each of $R_a$ and $R_b$ is straight or branched $C_1$-$C_{10}$ alkyl; and $R_c$ is straight or branched $C_1$-$C_{10}$ alkyl or cyanoethyl.

5. The compound of claim 4, wherein:

X is a $C_1$-$C_{100}$ straight or branched alkyl linking group, wherein one or more carbon atoms are optionally replaced with nitrogen, oxygen or sulfur, or a combination thereof; and Y is controlled pore glass (CPG) or polystyrene.

6. The compound of claim 4, wherein:
X is a $C_1$-$C_{100}$ straight or branched alkyl linking group wherein one or more carbon atoms are optionally replaced with nitrogen, oxygen or sulfur, or a combination thereof; and
Y is

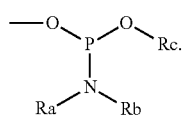

7. A compound represented by formula 7:

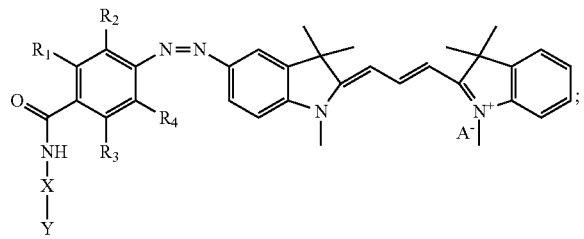

(Formula 7)

wherein:
A⁻ is an anion selected from Cl⁻, Br⁻, I⁻, $ClO_4^-$, $BF_4^-$ or $CH_3COO^-$;
each of $R_1$, $R_2$, $R_3$ and $R_4$ is independently hydrogen, halogen, $NO_2$, $SO_3R$, $SO_2N(R)_2$, CN, CNS, $C_1$-$C_{10}$ alkoxy, $C_1$-$C_{10}$ alkyl, aryl, or heteroaryl; or
$R_1$ and $R_2$ together or $R_3$ and $R_4$ together form a five- or six-membered ring, wherein said five- or six-membered ring is optionally substituted with halogen, $NO_2$, $SO_3R$, $SO_2N(R)_2$, CN, CNS, ($C_1$-$C_{10}$)alkoxy, $C_1$-$C_{10}$ alkyl, aryl, or heteroaryl;
X is a $C_1$-$C_{100}$ straight or branched alkyl linking group, wherein one or more carbon atoms are optionally replaced with nitrogen, oxygen or sulfur, or a combination thereof; and
Y is controlled pore glass (CPG), polystyrene or

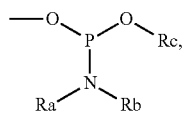

wherein each of $R_a$ and $R_b$ is straight or branched $C_1$-$C_{10}$ alkyl; and $R_c$ is straight or branched $C_1$-$C_{10}$ alkyl or cyanoethyl.

8. The compound of claim 7, wherein:
X is a $C_1$-$C_{100}$ straight or branched alkyl linking group, wherein one or more carbon atoms are optionally replaced with nitrogen, oxygen or sulfur, or a combination thereof; and
Y is controlled pore glass (CPG) or polystyrene.

9. The compound of claim 7, wherein:
X is a $C_1$-$C_{100}$ straight or branched alkyl linking group, wherein one or more carbon atoms are optionally replaced with nitrogen, oxygen or sulfur, or a combination thereof; and Y is

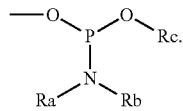

10. The compound of claim 1 further having an oligonucleotide linked through Y to the compound of Formula 4.
11. The compound of claim 10 wherein the compound of Formula 4 is linked to the 3'-terminus of the oligonucleotide.
12. The compound of claim 10 wherein the compound of Formula 4 is linked to the 5'-terminus of the oligonucleotide.
13. The compound of claim 4 further having an oligonucleotide linked through Y to the compound of Formula 6.
14. The compound of claim 13 wherein the compound of Formula 6 is linked to the 3'-terminus of the oligonucleotide.
15. The compound of claim 13 wherein the compound of Formula 6 is linked to the 5'-terminus of the oligonucleotide.
16. The compound of claim 7 further having an oligonucleotide linked through Y to the compound of Formula 7.
17. The compound of claim 16 wherein the compound of Formula 7 is linked to the 3'-terminus of the oligonucleotide.
18. The compound of claim 16 wherein the compound of Formula 7 is linked to the 5'-terminus of the oligonucleotide.
19. A method for synthesizing an oligonucleotide containing a fluorescent quenching compound comprising:
  a) treating a composition containing a derivatized aromatic ring with $NaNO_2$ to form a diazonium salt;
  b) reacting the diazonium salt with a composition comprising a 1,3,3-trimethyl-2-methyleneindoline to form a product comprising an azo group; and
  c) covalently attaching the product into an oligonucleotide, thereby forming the oligonucleotide containing a fluorescent quenching compound.
20. A compound represented by Formula 8:

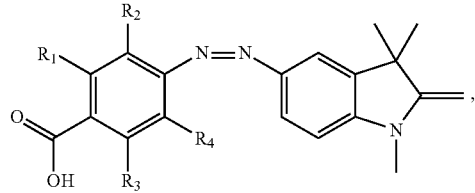

(Formula 8)

wherein:
each of $R_1$, $R_2$, $R_3$ and $R_4$ is independently hydrogen, halogen, $NO_2$, $SO_3R$, $SO_2N(R)_2$, CN, CNS, ($C_1$-$C_{10}$) alkoxy, $C_1$-$C_{10}$ alkyl, aryl, or heteroaryl; or
$R_1$ and $R_2$ together or $R_3$ and $R_4$ together form a five- or six-membered ring, wherein said five- or six-membered ring is optionally substituted with halogen, $NO_2$, $SO_3R$, $SO_2N(R)_2$, CN, CNS, ($C_1$-$C_{10}$)alkoxy, $C_1$-$C_{10}$ alkyl, aryl, or heteroaryl; and
R is H or $C_1$-$C_{10}$ alkyl.
21. A compound represented by formula 9:

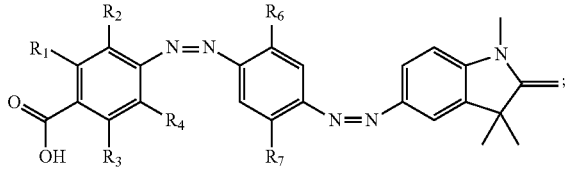

Formula 9 wherein:
- each of $R_1$, $R_2$, $R_3$ and $R_4$ is independently hydrogen, halogen, $NO_2$, $SO_3R$, $SO_2N(R)_2$, CN, CNS, ($C_1$-$C_{10}$) alkoxy, $C_1$-$C_{10}$ alkyl, aryl, or heteroaryl; or
- $R_1$ and $R_2$ together or $R_3$ and $R_4$ together form a five- or six-membered ring, wherein said five- or six-membered ring is optionally substituted with halogen, $NO_2$, $SO_3R$, $SO_2N(R)_2$, CN, CNS, ($C_1$-$C_{10}$)alkoxy, $C_1$-$C_{10}$ alkyl, aryl, or heteroaryl;
- R is H or $C_1$-$C_{10}$ alkyl; and
- each of $R_6$ and $R_7$ is independently hydrogen, methyl, or methoxy.

22. A compound represented by formula 10:

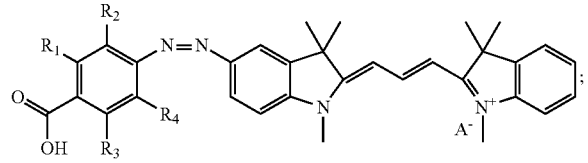

(Formula 10)

wherein:
- $A^-$ is an anion selected from $Cl^-$, $Br^-$, $I^-$, $ClO_4^-$, $BF_4^-$ or $CH_3COO^-$;
- each of $R_1$, $R_2$, $R_3$ and $R_4$ is independently hydrogen, halogen, $NO_2$, $SO_3R$, $SO_2N(R)_2$, CN, CNS, $C_1$-$C_{10}$ alkoxy, $C_1$-$C_{10}$ alkyl, aryl, or heteroaryl; or
- $R_1$ and $R_2$ together or $R_3$ and $R_4$ together form a five- or six-membered ring, wherein said five- or six-membered ring is optionally substituted with halogen, $NO_2$, $SO_3R$, $SO_2N(R)_2$, CN, CNS, ($C_1$-$C_{10}$)alkoxy, $C_1$-$C_{10}$ alkyl, aryl, or heteroaryl; and
- R is H or $C_1$-$C_{10}$ alkyl.

23. The compound of claim 10, wherein the oligonucleotide further comprises a covalently attached fluorescent dye.

24. The compound of claim 1, wherein the compound is 5-(4-(4-Carboxamidophenylazo)-2,5-dimethoxyphenylazo)-1,3,3-trimethyl-2-methyleneindoline derivatized controlled pore glass.

* * * * *

UNITED STATES PATENT AND TRADEMARK OFFICE
CERTIFICATE OF CORRECTION

PATENT NO.        : 7,956,169 B1
APPLICATION NO.   : 12/816527
DATED             : June 7, 2011
INVENTOR(S)       : Andrei Laikhter et al.

Page 1 of 1

It is certified that error appears in the above-identified patent and that said Letters Patent is hereby corrected as shown below:

In Column 29, Claim 1, line 2, delete the chemical compound and insert:

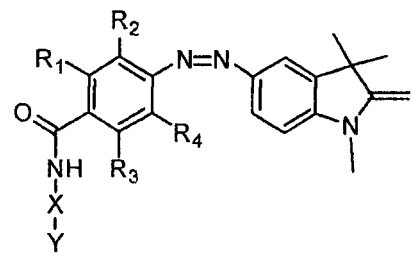

--                                          --

Signed and Sealed this
Sixteenth Day of August, 2011

David J. Kappos
*Director of the United States Patent and Trademark Office*

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(10)
<223> OTHER INFORMATION: All t's are Deoxyribonucleotides
<220> FEATURE:
<221> NAME/KEY: misc_feature
<222> LOCATION: 10
<223> OTHER INFORMATION: Thymidine at position 10 is modified by
      5-(4-(4-carboxyphenylazo)-2,5-dimethoxyphenylazo)-
```

-continued 1,3,3-trimethyl-2-methyleneindoline

<400> SEQUENCE: 1
tttttttttt                                                                              10

<210> SEQ ID NO 2
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(10)
<223> OTHER INFORMATION: All t's are Deoxyribonucleotides
<220> FEATURE:
<221> NAME/KEY: misc_feature
<222> LOCATION: 10
<223> OTHER INFORMATION: Thymidine at position 10 is modified by
      5-(2-nitro-4-carboxyphenylazo)-1,3,3-trimethyl-2-m
      ethyleneindoline

<400> SEQUENCE: 2
tttttttttt                                                                              10

<210> SEQ ID NO 3
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(28)
<223> OTHER INFORMATION: All c's, a's, g's and t's are
      Deoxyribonucleotides
<220> FEATURE:
<221> NAME/KEY: misc_feature
<222> LOCATION: 1
<223> OTHER INFORMATION: Thymidine at position 1 is modified by
      5-carboxyfluorescein
<220> FEATURE:
<221> NAME/KEY: misc_feature
<222> LOCATION: 28
<223> OTHER INFORMATION: Deoxycytidine at position 28 is modified by
      5-(4-(4-carboxyphenylazo)-2,5-dimethoxyphenylazo)-
      1,3,3-trimethyl-2-methyleneindoline

<400> SEQUENCE: 3
tgccatcctg gattccagaa gattcaac                                                           28

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(27)
<223> OTHER INFORMATION: All c's, a's, g's and t's are
      Deoxyribonucleotides
<220> FEATURE:
<221> NAME/KEY: misc_feature
<222> LOCATION: 1
<223> OTHER INFORMATION: Deoxyadenosine at position 1 is modified by
      5-carboxyfluorescein
<220> FEATURE:

-continued

```
<221> NAME/KEY: misc_feature
<222> LOCATION: 27
<223> OTHER INFORMATION: Deoxyguanosine at position 27 is modified by
      5-(4-(4-carboxyphenylazo)-2,5-dimethoxyphenylazo)-
      1,3,3-trimethyl-2-methyleneindoline

<400> SEQUENCE: 4
aggaaaacag ccaccaggtg aaggagg                                      27
```